United States Patent [19]

Bauer et al.

[11] 4,026,951

[45] May 31, 1977

[54] PROCESS FOR THE PRODUCTION OF ANETHOLE

[75] Inventors: Kurt Bauer, Holzminden; Reiner Mölleken, Golmbach Ortsteil Warbsen, both of Germany

[73] Assignee: Haarmann & Reimer GmbH, Holzminden, Germany

[22] Filed: Apr. 14, 1975

[21] Appl. No.: 568,091

[30] Foreign Application Priority Data

Apr. 19, 1974 Germany .......................... 2418974

[52] U.S. Cl. .......................... 260/612 D; 260/613 R
[51] Int. Cl.² .......................... C07C 41/00
[58] Field of Search ....... 260/612 D, 613 D, 613 R, 260/624 B

[56] References Cited

UNITED STATES PATENTS

| 2,373,982 | 4/1945 | Sturrock et al. | 260/624 B X |
| 2,560,173 | 7/1951 | Johnson et al. | 260/613 R X |
| 2,591,651 | 4/1952 | Young | 260/613 R X |
| 2,829,175 | 4/1958 | Bowman et al. | 260/613 R X |
| 2,862,976 | 12/1958 | Dubbs et al. | 260/613 R X |
| 2,979,534 | 4/1961 | Petropoulos et al. | 260/624 B X |

OTHER PUBLICATIONS

Braun et al., Ann., vol. 472 (1929) 72-79.
Quelet, Compt. Rend, vol. 202 (1936) 956-958.

*Primary Examiner*—Bernard Helfin
*Attorney, Agent, or Firm*—Burgess, Dinklage & Sprung

[57] ABSTRACT

The invention relates to a new process for the production of anethole (4-methoxy propen-1-yl benzene), wherein anisole is condensed with propionaldehyde in the presence of an acid catalyst and the resulting condensation product is subsequently split in the presence of an acid at a temperature in the range from 100° to 300° C.

9 Claims, No Drawings

PROCESS FOR THE PRODUCTION OF ANETHOLE

This invention relates to a new process for the production of anethole (4-methoxy propen-1-yl benzene).

It has been found that anethole can be obtained in a simple, economic manner by initially condensing anisole with propionaldehyde in the presence of an acid catalyst and subsequently splitting the resulting condensation product in the presence of an acid at a temperature in the range from 100° to 300° C.

For the first stage of the reaction, namely the condensation reaction, the starting materials, anisole and propionaldehyde, are used in a molar ratio of 1:1 to 15:1, preferably in a molar ratio of 2:1 to 10:1 and, more especially, in a molar ratio of 2:1 to 6:1.

One particular feature of the process according to the invention is that the propionaldehyde can be replaced completely or partly by the anethole isomers accumulating as secondary products in the production of anethole by the process according to the invention. In this way, there is no accumulation of unusable secondary products in the process according to the invention.

Acid catalysts which may be used for the condensation reaction are in particular, medium-strength to strong proton acids, acid ion exchangers, acid anhydrides of inorganic acids or Lewis acids.

The following are mentioned as examples of medium-strength to strong proton acids: strong to medum-strength inorganic acids such as: sulphuric acid, acids of phosphorus, for example orthophosphoric acid, metaphosphoric acid, polyphosphoric acid, phosphortungstic acid or phosphormolybdic acid, also hydrohalic acids, for example hydrochloric acid and hydrobromic acid, and amidosulphonic acid; strong organic acids such as sulphonic acids, for example p-toluene sulphonic acid, p-methoxy benzene sulphonic acid, also oxalic acid, trifluoroacetic acid and picric acid.

The following are mentioned as examples of suitable acid ion exchangers: inorganic cation exchangers such as natural hydrosilicates of aluminium, for example montmorillonites, glauconites or zeolites, prepared commercial-grade aluminium hydrosilicates, for example hydrosilicates of aluminium prepared by treatment with acids (cf. Ullmanns Enzyklopadie der technischen Chemie, Vol. 8, 3rd Edition, 1957, page 801); commercial-grade mineral cation exchangers obtained from silicates, such as kaolin or feldspar, and clay minerals such as bauxite, silica and sodium hydroxide or soda (cf. Ullamnn Vol. 8, 3rd Edition 1957, page 802) the aluminium compounds also being replaceable either wholly or in part by iron, tin, lead, zirconium, titanium, chromium, tungsten, vanadium or boron compounds (cf. Ullmann, Vol. 8, 3rd Edition, 1957, page 802); carbon-based exchangers activated with sulphuric acid; or organic cation exchangers, for example polycondensation resins based on phenol-formaldehyde, or polymerisation resins based on styrene or styrenes substituted by alkyl, alkoxy or halogen groups and containing carboxyl or phosphoric acid groups, also copolymers of polystyrene, acrylic acid, methacrylic acid or meleic acid containing sulphonic acid, carboxyl or phosphoric acid groups (cf. Ullmann, Vol. 8, 3rd Edition, 1957, pages 806–810).

Acid anhydrides of inorganic acids are in particular, solid acid anhydrides of inorganic non-oxidising acids, for example phosphorus pentoxide.

The following are mentioned as examples of Lewis acids: aluminium chloride, antimony trichloride, antimony pentachloride, iron (III) chloride, boron fluoride, zinc chloride or phosphorus halides such as $PCl_3$ or $PCl_5$.

It is also possible to use mixtures of the above-mentioned catalysts.

The acid catalyst are preferably used in quantities of from 0.001 10% by weight, especially in quantities of from 0.1 to 5% by weight and, more especially, in quantities of from 0.1 to 3% by weight, based on the weight of propionaldehyde used.

The temperatures for the condensation reaction are in the range from - 10° to 150° C, preferably in the range from 50° to 150° C and, more especially, in the range from 120° to 150° C.

The condensation reaction may be carried out under normal pressure, excess pressure or in vacuo.

There is generally no need to use a solvent for the condensation reaction, because the anisole used as one of the starting materials also serves as a solvent. However, the reaction is not adversely affected by the addition of an inert solvent, provided that the necessary reaction temperatures are attained.

The condensation reaction may be carried out either continuously or in batches. When it is carried out in batches, it is possible for example to introduce the reaction components and the catalyst in any order into a condenser-equipped apparatus, followed by heating while stirring to the reaction temperature indicated. The reaction mixture is then kept at that temperature until the anisole has completely reacted.

In the cases where the reaction is carried out continuously, the mixture of anisole, propionaldehyde and catalyst may be metered into the reactor heated to the reaction temperature.

The condensation product, consisting essentially of p,p'-o,p' - and o,o' - dimethoxy diphenyl propane, may be purified by conventional methods, for example by distillation, crystallisation or extraction.

The reaction mixture which accumulates during the condensation reaction may be used for the following splitting reaction either as such or following separation of the catalyst and excess anisole, if any. The catalyst may be separated off by known methods. For example, liquid acids may be washed out of the reaction mixture with water or neutralised with alkalis, in which case the salts obtained may also be washed out with water. Acid solid catalysts may be removed by filtration or by centrifuging.

It is possible, although not necessary, to separate the mixture, which accumulated during condensation, of the various isomeric dimethoxy diphenyl propanes, for example, 1,1-di-(4-methoxy phenyl)-propane, 1,1-di-(2methoxy phenyl)-propane or 1-(2-methoxy phenyl)-1-(4-methoxy phenyl)-propane, into the individual o- and p-isomers, for example by crystallisation or fractional distillation, before the splitting reaction is carried out.

In the splitting reaction, the dimethoxy diphenyl propanes are split into p- and o-anethole and anisole in the presence of catalytic quantities of acids.

Catalysts which are suitable for the splitting reaction are acids which are involatile under the reaction conditions or which do not lose their catalytic activity through secondary reactions. The following are mentioned as examples of such acids: strong to medium-strength proton acids, for example acids of phosphorus such as orthophosphoric acid, metaphosphoric acid, pyrophosphoric acid, phosphortungstic acid, phosphormolybdic acid; acid alkyl, cycloalkyl and aralkyl esters of phosphoric acid such as ethyl or diethyl, hexyl, cyclohexyl, benzyl, octyl, ethyl hexyl phosphates; thiosulphuric acid, dischloroacetic acid, amidosulphonic acid, sulphuric acid, chlorosulphonic acid, perchloric acid, sulphonic acids, for example ethane sulphonic acid, benzene sulphonic acid, toluene suphonic acid; strongly acid organic and inorganic cation exchangers or supporting substances impregnated with strong acids. Mixtures of the aforementioned acids may also be used. It is preferred to use acids of phosphorus, especially orthophosphoric acid or acid esters thereof.

The reaction temperatures for the splitting reaction are in the range from about 100° to 300° C, preferably in the range from 150° to 230° C and, more especially, in the range from 160° to 200° C.

Splitting is carried out under a pressure of from about 0.1 to about 760 Torr, preferably under a pressure of from 0.1 to 100 Torr and, more especially, under a pressure of from 0.1 to 20 Torr.

The splitting reaction may be carried out by mixing dimethoxy diphenyl propanes or the condensation product obtained in the first stage of the reaction with the acid catalyst in a vacuum-tight apparatus equipped with a metering unit and a descending condenser. The catalyst is preferably used in a quantity of from 0.001 to 10% by weight, especially in a quantity of from 0.1 to 5% by weight and, more especially, in quantity of from 0.1 to 3% by weight, based on the weight of dimethoxy diphenyl propane used. The apparatus is evacuated and the reaction mixture heated with stirring to the reaction temperature. When the reaction temperature is reached, the products of the splitting reaction, anisole and anethole, begin to distil off. The splitting reaction is continued until no more products of that reaction distil over.

In one particularly advantageous embodiment of the process according to the invention, anisole is mixed with the catalyst and the resulting mixture is heated in a reaction vessel, provided with a descending condenser and a receiver, to a reaction temperature which is above the boiling point of water and below the boiling point of anisole under the pressure applied. The following pressure-temperature conditions have proved to be particularly effective: pressure 100 Torr to 760 Torr, temperature 100° to 150° C. After this reaction temperature has been reached, the propionaldehyde is introduced into the anisole-catalyst mixture in the amount as it is consumed, whilst the water formed during the reaction is continuously removed from the reaction mixture either by the addition of water-binding reagents, such as sodium sulphate, phosphorus pentoxide or silica gel, or preferably by distillation.

Where this procedure is adopted, it is surprisingly not propionaldehyde, but almost exclusively water, which distils over although the boiling point of propionaldehyde at 46.5° C is much lower than that of water. It has been found that, where the reaction is carried out under these conditions, formation of the condensation product is almost quantitative, whilst the formation of secondary products, such as 2-methyl-pent-2-en-1-al, and its condensation products, is almost completely suppressed.

The mixture of dimethoxy diphenyl propanes and catalyst thus obtained is heated to the necessary splitting- reaction temperature in a reaction vessel equipped with a descending condenser, the temperature of the splitting reaction being selected so that it is above the boiling point of the starting material under the reaction pressure applied. Under these conditions, the anethole formed during the splitting reaction immediately distils off and accumulates in a high yield together with anisole and entrained starting material. The necessary rapid separation of the anethole formed from the reaction mixture may also be carried out by other methods known per se, for example by carrier-vapour distillation or by distillation through thin-layer evaporators. These embodiments are particularly suitable for continuous working.

The distillate which accumulates during the splitting process according to the invention predominantly contains cis- and trans- isomers of p-anethole, together with anisole and in addition, in case where an o- p-isomer mixture of dimethoxy diphenyl propanes has been used as starting material for the splitting reaction, cis- and trans-o-anethole (o-methoxy propenyl benzene) as well. These compounds may be separated from one another by conventional methods, for example by fractional distillation, the cis- and trans-isomers of p-anethole and, optionally, of o-anethole as well being obtainable in pure form. The unwanted reaction products, such as cis- and trans-o-anethole and cis-p-anethole may be returned to the condensation stage to replace all or some of the starting material, propionaldehyde.

The process according to the invention is of particular importance for the preparation of trans-p-anethole. This compound smells of aniseed, has a sweet taste and is used in odorant and flavouring industries, for example in the production of liqueurs and in cosmetic preparations. p-anethole is used in colour photography (Rompp's Chemie-Lexikon, Vol. 1, page 182, Franksche Verlagsbuchhandlung, 7th Edition, 1973), and also as an intermediate products, for example in the production of anisaldehyde.

The process according to the invention is distinguished from conventional processes for the production of anethole from star anise oil or by base-catalysed rearrangement from 3-(4-methoxy phenyl)-1-propene, (see E. Gildemeister, "Die atherischen Ole", 4th Ed., 1966, Vol. IIId page 419), by its simplicity and economy. By virtue of the process according to the invention, anethole is synthesised on an industrial scale from readily obtainable starting materials. One particular advantage of the process according to the invention is that the anethole isomers which accumulate as secondary products, for which there is no other commercial application, can be repeatedly recycled to the condensation reaction stage of the process according to the invention where they are recondensed with anisole, so that there is no accumulation of any unusuable secondary products in the process according to the invention. It is surprising that splitting with the acid catalysts should lead to the required product because anethole is dimerised or polymerised by the same catalyst.

The invention is illustrated by the following Examples:

EXAMPLE 1 a. Condensation

A mixture of 432 g (4 mols) of anisole and 4 g of concentrated $H_3PO_4$ was heated to 150° C in a reaction vessel equipped with a stirrer, metering unit and descending condenser. After the afore mentioned temperature has been reached, 58 g (1 mol) of propionaldehyde were added through the metering unit over a period of 1.5 hours and, at the same time, the water of reaction formed distilled off. On completion of the addition, the upper phase of the reaction mixture was decanted from the phosphoric acid precipitated and the excess anisole removed from the reaction mixture by distillation, leaving 251.8 g of condensation product consisting of p,p'-, o,p'- and o,o'-1,1-dimethoxy diphenyl propane. The yeld amounted to 98.4%, based on the propionaldehyde used.

b. Splitting

For splitting, 100 g of 1,1-dimethoxy diphenyl propane from the condensation stage (a) were heated to 200° C in a distillation apparatus fitted with a Claisen attachment, followed by the addition of 0.5 g of concentrated phosphoric acid. The products formed during the splitting reaction distilled off over a period of 15 minutes at about 5 to 30 Torr. According to analysis by gas chromatography, the distillate (95.5 g) contained 32.7 g of unsplit 1,1-dimethoxy diphenyl propane, 24.1 g of trans-p-anethole, 9.1 g of trans-o- and cis-p-anethole and 1.2 g of p-propyl anisole, corresponding to a yeld of 91.4% of anetholes, based on reacted condensate.

Pure trans-p-anethole was obtained from the product of splitting by fractional distillation: b.p. 110° C/10 Torr.

EXAMPLE 2

A mixture of 324 g (3 mols) of anisole and 4 g of concentrated $H_3PO_4$ was heated to 150° C in a 500 ml capacity reaction vessel equipped with a thermometer, stirrer and dropping funnel. After the above-mentioned temperature had been reached, 64 g (0.432 mol) of o-anethole (2-methoxy-propen-l-yl benzene) were introduced into the throughly stirred anisole/phosphoric acid mixture over a period of 1 hour, followed by stirring for 1 hour at the same temperature. The excess anisole was then distilled off at 50° C/5 Torr, leaving 110 g of a condensation product consisting predominantly of the o,p'-isomers of 1,1-dimethoxy diphenyl propane. The yield was substantially quantitative.

For splitting, the condensate was heated to 200° C in the presence of the phosphoric acid left in the condensate. The products of splitting formed, anisole and the o-p-anetholes, distil off over a period of 10 minutes at 10 Torr.

Distillation of 55 g of 1,1-dimethoxy diphenyl propane gave 17.8 g of a distillate which contained 14% of trans-p-anethole according to analysis by gas chromatography. 24.2 g of condensate were recovered.

The Example illustrates that o-anethole can be converted by the process according to the invention into trans-p-anethole.

We claim:
1. A process for the production of anethole which comprises splitting 1,1-(dimethoxyphenyl) propane by heating at a temperature in the range from 100° to 300° C in the presence of an acid catalyst for the splitting, to form said anethole and recovering said anethol.

2. A process as claimed in claim 1, wherein said temperature is in the range from 150° to 230° C.

3. A process of claim 1, wherein said dimethoxy diphenyl propane is produced in a preliminary reaction by contacting anisole with anethole isomers in the presence of acid catalyst for the preliminary reaction, at a temperature and for a time sufficient to form said dimethoxy diphenyl propane.

4. A process as claimed in claim 1, wherein the acid catalyst used for the thermal splitting reaction is an acid of phosphorus or an acid ester of phosphorus.

5. A process as claimed in claim 1, wherein the thermal splitting is carried out under reduced pressure.

6. A process as claimed in claim 1, wherein the dimethoxy-diphenyl propane comprises p, p'-, o,p'-, and o, o'-dimethoxy diphenyl propane.

7. A process as claimed in claim 1, wherein the anethole produced predominately contains cis- and trans- isomers of p-anethole.

8. A process as claimed in claim 1, wherein the anethole produced contains cis- and trans- isomers of p-anethole, and cis- and trans- isomers of o-anethole, the trans- isomer of p-anethole, is separated from the anethole produced, and the cis-p-anethole and cis- and trans-o- anethole are introduced into the preliminary reaction.

9. A process as claimed in claim 1, wherein the anethole produced contains cis- and trans- isomers of p-anethole, and pure p-anethole is separated from the anethole produced.

* * * * *

UNITED STATES PATENT AND TRADEMARK OFFICE
CERTIFICATE OF CORRECTION

PATENT NO. : 4,026,951
DATED : May 31, 1977
INVENTOR(S) : Kurt Bauer, et al

It is certified that error appears in the above—identified patent and that said Letters Patent are hereby corrected as shown below:

Column 1, line 32, after "acid," insert --pyrophosphoric acid,--.

Column 1, line 63, "meleic" should be --maleic--.

Column 3, line 6, "dischloracetic" should be --dichloroacetic--.

Signed and Sealed this sixteenth Day of August 1977

[SEAL]

Attest:

RUTH C. MASON
Attesting Officer

C. MARSHALL DANN
Commissioner of Patents and Trademarks